United States Patent [19]
Lucas

[11] Patent Number: 5,935,285
[45] Date of Patent: *Aug. 10, 1999

[54] METHOD FOR INSPECTING MANUFACTURED ARTICLES

[75] Inventor: Philip J. Lucas, Lakewood, Colo.

[73] Assignee: Coors Brewing Company, Golden, Colo.

[*] Notice: This patent issued on a continued prosecution application filed under 37 CFR 1.53(d), and is subject to the twenty year patent term provisions of 35 U.S.C. 154(a)(2).

[21] Appl. No.: 09/001,215

[22] Filed: Dec. 30, 1997

[51] Int. Cl.$^6$ .............................. C03B 9/00; G01N 21/90
[52] U.S. Cl. ................... 65/29.12; 65/29.18; 65/158; 356/239.4; 356/240.1; 198/339.1; 348/127; 382/142
[58] Field of Search ............................ 65/29.12, 29.14, 65/29.18, 158; 73/865.8; 356/239.1, 239.4, 240.1; 198/339.1; 382/142; 250/559.4; 264/408, 406; 364/473.02; 348/127

[56] References Cited

U.S. PATENT DOCUMENTS

| | | | |
|---|---|---|---|
| 3,387,551 | 6/1968 | Hughes | 98/88 |
| 3,708,679 | 1/1973 | Stock et al. | 250/223 R |
| 3,767,374 | 10/1973 | Iacovazzi et al. | 65/165 |
| 3,886,356 | 5/1975 | Gomm et al. | 250/223 |
| 4,004,904 | 1/1977 | Fergusson | 65/158 |
| 4,019,819 | 4/1977 | Lodzinski | 356/73 |
| 4,026,656 | 5/1977 | Kusz et al. | 356/51 |
| 4,306,835 | 12/1981 | Hurley | 415/118 |
| 4,332,606 | 6/1982 | Gardner | 65/158 |
| 4,402,721 | 9/1983 | Ericson et al. | 65/29 |
| 4,431,436 | 2/1984 | Lulejian | 65/159 |
| 4,492,476 | 1/1985 | Miyazawa | 356/428 |
| 4,494,656 | 1/1985 | Shay et al. | 209/524 |

(List continued on next page.)

FOREIGN PATENT DOCUMENTS

| | | |
|---|---|---|
| 2 094 530 | 9/1982 | United Kingdom . |
| 2 179 648 | 3/1987 | United Kingdom . |

OTHER PUBLICATIONS

Continuing Patent Application Serial Number 08/698,591 filed Aug. 16, 1996 for "Method for Measurement of Light Transmittance" of Hidalgo et al.

Continuing Patent Application Serial No. 08/831,384 filed Apr. 1, 1997, for "Hot Bottle Inspection Apparatus and Method" of Burns, et al.

Continuing Patent Application Serial Number 08/898,535 filed Jul. 22, 1997, for "Hot Bottle Inspection Apparatus" of Burns, et al.

(List continued on next page.)

Primary Examiner—Steven P. Griffin
Attorney, Agent, or Firm—Klaas, Law, O'Meara & Malkin, P.C.; Michael A. Goodwin

[57] ABSTRACT

A method is disclosed for detecting the cycling of a manufacturing machine, such as a bottle manufacturing machine, without the need for a mechanical detection device. An imaging device, which may also be used to inspect products manufactured by the manufacturing machine, monitors a portion of the manufacturing machine in order to determine when the machine cycles. Also disclosed is a method for correlating a product being inspected to its point of origin, e.g., correlating a bottle to its mold cavity of origin in the case of a bottle manufacturing machine. The manufacturing machine cycle time is divided by the number of origin points, e.g., the number of bottle mold cavities in the case of a bottle manufacturing machine, to derive a product interval time. The arrival time of each product being inspected may then be divided by the product interval time in order to predict the point of origin from which the product originated.

18 Claims, 6 Drawing Sheets

Microfiche Appendix Included
(1 Microfiche, 47 Pages)

U.S. PATENT DOCUMENTS

| | | | |
|---|---|---|---|
| 4,500,203 | 2/1985 | Bieringer | 356/240 |
| 4,553,217 | 11/1985 | Daudt et al. | 364/560 |
| 4,599,099 | 7/1986 | Jones | 65/29 |
| 4,606,746 | 8/1986 | Keller | 65/29 |
| 4,608,072 | 8/1986 | Fenton | 65/79 |
| 4,614,531 | 9/1986 | Bishop et al. | 65/158 |
| 4,639,263 | 1/1987 | Kulikauskas | 65/158 |
| 4,649,503 | 3/1987 | Keller | 364/552 |
| 4,664,521 | 5/1987 | Scott et al. | 356/240 |
| 4,675,042 | 6/1987 | Taddei-Contreras et al. | 65/158 |
| 4,679,075 | 7/1987 | Williams et al. | 358/106 |
| 4,691,830 | 9/1987 | Ahl et al. | 209/523 |
| 4,694,158 | 9/1987 | Leser | 250/223 |
| 4,762,544 | 8/1988 | Davey | 65/29 |
| 4,915,237 | 4/1990 | Chang et al. | 209/524 |
| 4,948,956 | 8/1990 | Fukuchi | 250/223 |
| 4,997,769 | 3/1991 | Lundsgaard | 436/66 |
| 5,187,368 | 2/1993 | Galante et al. | 250/341 |
| 5,305,081 | 4/1994 | Gooch et al. | 356/240 |
| 5,345,309 | 9/1994 | Wertz et al. | 356/372 |
| 5,437,702 | 8/1995 | Burns et al. | 65/29.12 |
| 5,510,610 | 4/1996 | Baldwin | 250/223 B |
| 5,510,621 | 4/1996 | Goldman | 250/343 |
| 5,717,486 | 2/1998 | Burri et al. | 356/240 |
| 5,734,467 | 3/1998 | Lucas | 356/240 |

OTHER PUBLICATIONS

Continuation in Part Patent Application Serial Number 08/898,766 filed Jul. 23, 1997, for "Method for Measurement of Light Transmittance" of Hidalgo et al.

"The Hand Book of Glass Manufacture" vol. II compiled & edited by Fay V. Tooley & published by Books for Industry, Inc., and the Glass Industry Magazine Division of Magazines for Industry, Inc., 1974, Library of Congress No. 74–77520, at pp. 961–975.

"Method for Inspecting Translucent Objects Using Techniques", Philip J. Lucas, Inventor, Serial Number 09/000,808 Filing Date Dec. 30, 1997.

METHOD FOR INSPECTING MANUFACTURED ARTICLES

REFERENCE TO MICROFICHE APPENDIX

Reference is made to a Microfiche Appendix hereto, having a total of 1 microfiche and a total of 47 frames.

FIELD OF THE INVENTION

The present invention relates generally to a method for high speed inspection of manufactured articles and, more particularly, to a method for correlating each article inspected to its point of origin.

BACKGROUND OF THE INVENTION

It is well-known to convey articles on a high-speed conveyor subsequent to the manufacture of the articles. It is also well-known to inspect such articles as they pass by an inspection station located adjacent the high-speed conveyor.

In the case of glass bottles, for instance, the bottles are commonly formed in a bottle manufacturing machine, also commonly referred to in the industry as an "I.S. machine". A typical I.S. machine includes a plurality of bottle mold cavities which serve to form the bottles from molten or semi-molten glass. After being formed in the mold cavities of the I.S. machine, the bottles are generally transferred to an adjacent conveyor for transport to other bottle production areas. An inspection station which may, for example, comprise a bottle imaging system, may then be used to analyze the bottles being conveyed along the conveyor for dimensional attributes and/or for flaws which may exist in the bottles.

Examples of such imaging inspection systems are disclosed in U.S. Pat. 5,437,702 of Burns et al.; U.S. patent application Ser. No. 08/914,984 of Philip J. Lucas for HOT BOTTLE INSPECTION APPARATUS AND METHOD filed Aug. 20, 1997; U.S. patent application Ser. No. 08/526,897 of Philip J. Lucas for HOT BOTTLE INSPECTION APPARATUS AND METHOD filed Sep. 12, 1995; U.S. patent application Ser. No. 08/509,049, now U.S. Pat. No. 5,734,467, of Philip J. Lucas for HOT BOTTLE INSPECTION APPARATUS AND METHOD filed Jul. 31, 1995 and in U.S. patent application Ser. No. 09/000,808 of Philip J. Lucas for METHOD FOR INSPECTING TRANSLUCENT OBJECTS USING IMAGING TECHNIQUES, filed Dec. 30, 1997, the disclosures of which are all hereby incorporated by reference for all that is contained therein.

It is generally desirable to correlate each bottle inspected by the inspection station to the particular mold cavity within the I.S. machine that formed the bottle. In this manner, when a defect is detected by the inspection station, the mold cavity which formed the defective bottle may be determined and the mold cavity may then be repaired or replaced as appropriate.

In order to determine the mold cavity of origin for a bottle being inspected, it is first generally necessary to determine the timing of the I.S. machine. Prior inspection devices typically determine timing by using a mechanical detection device which sends a pulse signal to the inspection system, or to a remote computer attached thereto, each time that the bottle manufacturing machine complete a cycle. The use of a mechanical detection device is disadvantageous in that such mechanical detection devices generally require mechanical interaction with a moving part or parts of the bottle production machine and, thus, are subjected to mechanical wear. Because a mechanical detection device represents an additional component of the inspection system, the use of a mechanical detection device also adds to the expense of the overall inspection system.

Another problem with prior inspection systems involves the methodology used to correlate the inspected bottles to their respective mold cavities of origin within the I.S. machine. Typical inspection systems count the bottles which arrive at the inspection station. The bottle count, relative to the timing of the new cycle pulse signal described above, can generally be correlated to the mold cavity of origin of the bottle being inspected. A problem with this method is that bottles sometimes fall down or are missing from the conveyor. A fallen or missing bottle will not be counted in the bottle count and, thus, will cause the wrong mold cavity of origin to be assigned to bottles arriving at the inspection station subsequent to the fallen or missing bottle.

Accordingly, it would be desirable to provide a bottle inspection system and method which overcomes the problems associated with the prior art as generally described above.

SUMMARY OF THE INVENTION

The present invention is directed to a method of detecting the cycling of a manufacturing machine, such as a bottle manufacturing machine, without the need for a mechanical detection device. To monitor machine cycling, an imaging device is used to monitor the manufacturing machine. The imaging device may be of the type which is typically located adjacent the product conveyor for the purpose of imaging products as they are conveyed along the conveyor. According to the method, this imaging device may be used to additionally monitor a portion of the manufacturing machine in the background. The portion of the manufacturing machine monitored may be chosen to be a portion which moves only once per machine cycle. In this manner, a remote computer connected to the imaging device may analyze the image and detect when the manufacturing machine cycles. Thus, according to the present method, machine cycling can readily be detected without the need for a mechanical detection device.

The present invention is also directed to a method for correlating a product being inspected to its point of origin, e.g., correlating a bottle to its mold cavity of origin in the case of a bottle manufacturing machine. According to this method, the manufacturing machine cycle time is first measured. This cycle time is then divided by the number of origin points, e.g., the number of bottle mold cavities in the case of a bottle manufacturing machine, to derive a product interval time. The arrival time of each product being inspected may then be divided by the product interval time in order to predict the point of origin from which the product originated. Since this method uses timing, rather than a count, it is able to reliably predict the point of origin for products being inspected even if products are fallen or missing from the conveyor.

BRIEF DESCRIPTION OF THE DRAWING

An illustrative and presently preferred embodiment of the invention is shown in the accompanying drawing in which.

DETAILED DESCRIPTION OF THE INVENTION

Figure 1:
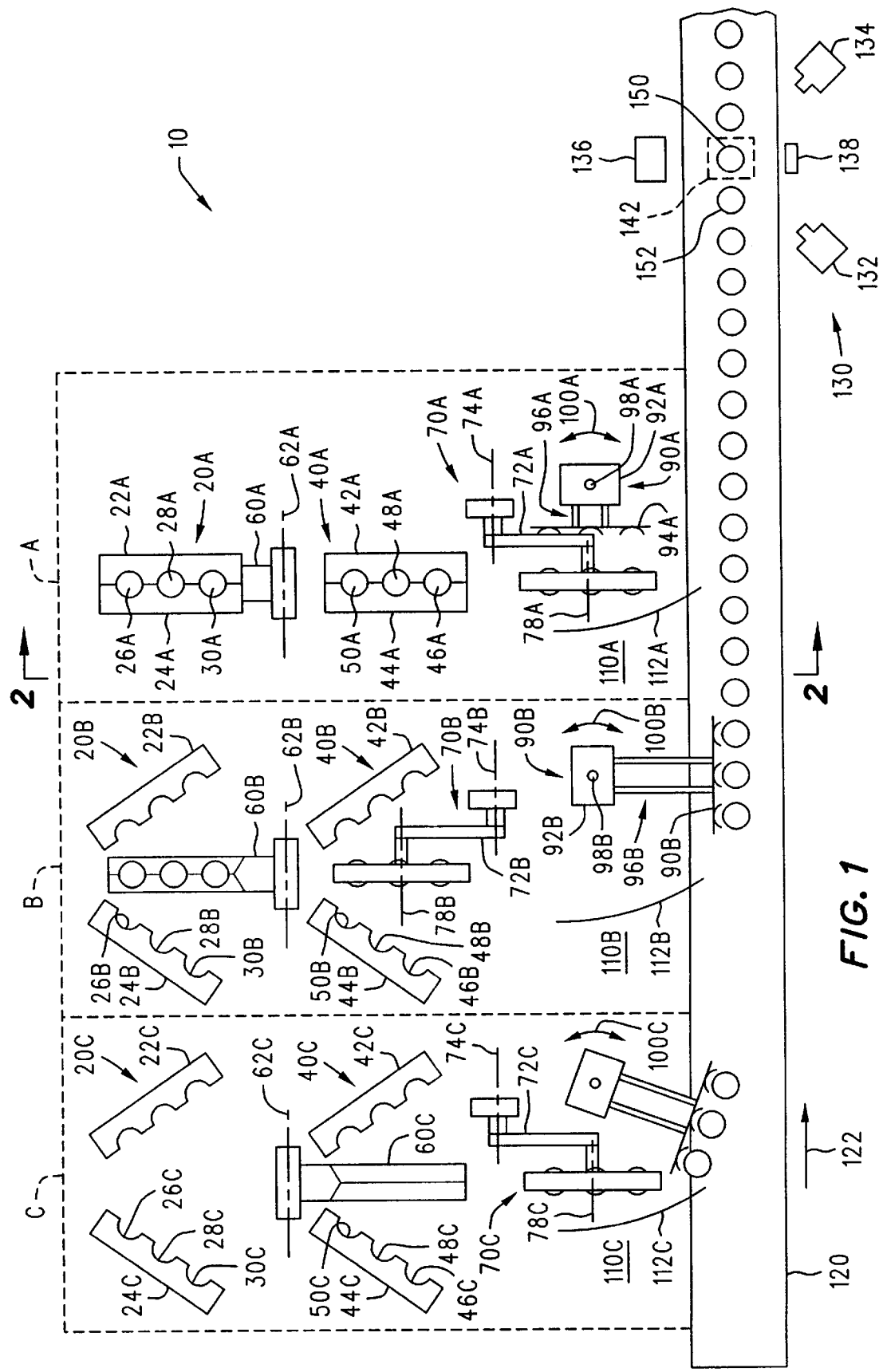
FIG. 1 is a top plan view of a bottle manufacturing machine, adjacent conveyor, and an inspection station located along the conveyor.

In general, the invention may pertain to a method of inspecting objects 150 with an imaging device 134 which is positioned adjacent a conveyor 120 along which the objects 150 are conveyed at a location downstream from a machine 10 for manufacturing the objects 150. The method includes the steps of obtaining an image 160 with the imaging device 134, wherein the image 160 includes at least one of the objects 150 in a first area of the image and includes at least a portion 72A of the machine 10 in a second area 170 of the image 160; performing an analysis of at least a portion of the second area 170 of the image 160; and determining an operating condition of the machine 10 based upon the analysis.

The invention may also pertain, in general, to a method of inspecting products 150 including the steps of providing a manufacturing machine 10 including a plurality of manufacturing stations 46A, 48A, 50A, 46B, 48B, 50B, 46C, 48C, 50C associated therewith; cycling the manufacturing machine 10 to produce a plurality of products 150, wherein one product is manufactured in each of the plurality of manufacturing stations 46A, 48A, 50A, 46B, 48B, 50B, 46C, 48C, 50C during each cycle of the manufacturing machine 10; transferring each of the plurality of products 150 to a conveyor 120 after being manufactured by the manufacturing machine 10; conveying each of the plurality of products 150 along the conveyor 120; inspecting at least one of the plurality of products 150 as it is being conveyed along the conveyor 120; determining the length of time taken for the manufacturing machine 10 to complete a cycle; and correlating the at least one of the plurality of products 150 to the manufacturing station 46A, 48A, 50A, 462, 48B, 50B, 46C, 48C, 50C which manufactured the at least one of the plurality of products 150 based upon the length of time.

Having thus described the method in general, further details thereof will now be specifically described.

It is well-known to convey articles on a high-speed conveyor subsequent to the manufacture of the articles. It is also well-known to inspect such articles as they pass by an inspection station located adjacent the high-speed conveyor.

In the case of glass bottles, for instance, the bottles are commonly formed in a bottle manufacturing machine 10, FIG. 1, also referred to in the industry as an "I.S. machine". Typically, an I.S. machine may contain a plurality of sections as illustrated in FIG. 1 by the sections A, B and C. Referring, for example, to section A in FIG. 1, it can be seen that each section may include a first mold 20A and a second mold 40A. First mold 20A, in turn, may include a right mold half 22A and a left mold half 24A. The right and left mold halves 22A, 24A may be hinged together such that they can swing apart to an open position as shown, for example with respect to the right and left mold halves 22B, 24B in section B of the bottle manufacturing machine 10. Each of the mold halves 22A and 24A include a plurality of semi-circular depressions such that, when the mold 20A is in its closed position, as shown, for example, with respect to Section A, three mold cavities 26A, 28A, 30A are formed.

Referring again to section A of FIG. 1, it can be seen that second mold 40A may include a right mold half 42A and a left mold half 44A. In a similar manner to the right and left mold halves 22A, 24A described above, the right and left mold halves 42A, 44A may be hinged together such that they can swing apart to an open position as shown, for example with respect to the right and left mold halves 42B, 44B in section B of the bottle manufacturing machine 10. Each of the mold halves 42A and 44A include a plurality of semi-circular depressions such that, when the mold 40A is in its closed position, as shown, for example, with respect to Section A, three mold cavities 46A, 48A, 50A are formed.

A first transfer arm 60A is arranged between the first mold 20A and the second mold 40A as shown. First transfer arm 60A is pivotable about the axis 62A in the directions indicated by the arrow line 64A, FIG. 2, such that the transfer arm 60A is moveable between a rearwardly disposed position, as illustrated with respect to sections A and B, and a forwardly disposed position, as illustrated with respect to section C.

Figure 2:
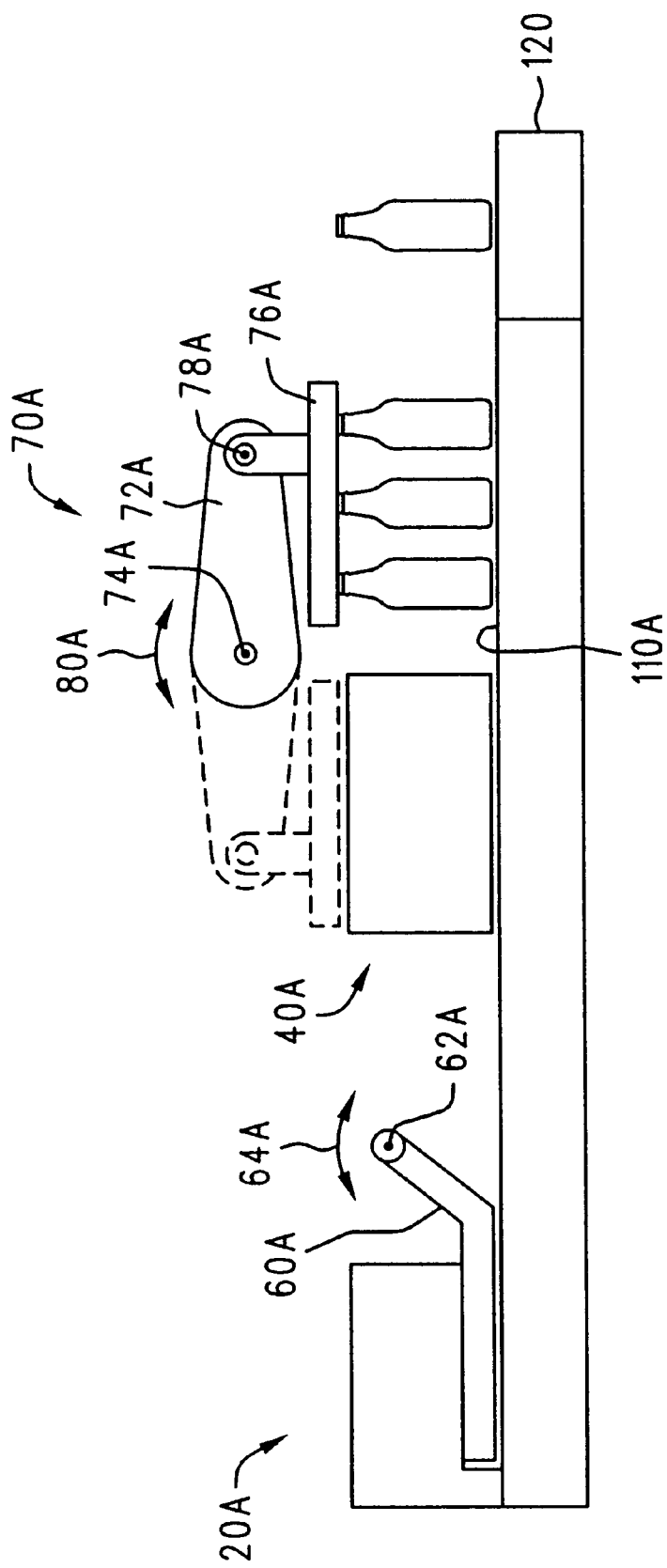
FIG. 2 is a cross-sectional elevation view taken along the line 2—2 of FIG. 1.

A second transfer arm assembly 70A is located on the opposite side of the second mold 40A from the first transfer arm 60A as shown. Second transfer arm assembly 70A may include pivot arm member 72A which is pivotable about an axis 74A. A gripper arm 76A may, in turn, be pivotally mounted to the pivot arm member 72A at a pivot axis 78A. With reference to FIG. 2, it can be appreciated that this arrangement allows the first transfer arm assembly 70A to move in the directions indicated by the arrow line 80A in FIG. 2 between a forward position, as shown with respect to sections A and C of FIG. 1 and as shown in solid lines in FIG. 2, and a rearward position, as shown with respect to section B of FIG. 1 and as shown in phantom in FIG. 2.

Referring again to FIG. 1, a swing arm assembly 90A is located adjacent the forward position of the second transfer arm assembly 70A. Swing arm assembly 90A may include a main body portion 92A. A bottle engaging member 94A may be attached to the main body portion 92A via a pair of extendable struts 96A as shown. Main body portion 92A, along with the attached bottle engaging member 94A, is pivotable about a pivot axis 98A in the directions indicated by the arrow line 100A between a first position, as shown with respect to section A of FIG. 1 and a second position as shown with respect to section B of FIG. 1. The extendable struts 96A and, thus, the attached bottle engaging member 94A are moveable relative to the main body portion 92A between a retracted position, as shown with respect to section A of FIG. 1, and an extended position, as shown with respect to sections B and C of FIG. 1.

It is noted that, although only section A of the bottle manufacturing machine 10 has been described in detail, each of the sections A, B, and C in FIG. 1 are substantially identical with like reference numerals denoting like components. It is further noted that, for illustration purposes, only three sections are shown in FIG. 1. A typical bottle forming machine, such as the bottle forming machine 10, however, might actually have between six and ten sections.

To begin a bottle making cycle with the bottle manufacturing machine 10, the first mold 20 is placed in its closed position with the first transfer arm 60 located beneath the mold, as shown with reference to section A of FIG. 1 and FIG. 2. Molten or semi-molten glass slugs, sometimes also referred to in the industry as "gobs", are then fed through chutes, not shown, into the first mold cavities 26, 28, 30, FIG. 1. A bottom former, not shown, may then be moved over the top of the mold cavities 26, 28, 30 in order to force the gobs into the shape of the mold cavities 26, 28, 30. The resulting formed gobs are commonly referred to in the industry as "preforms".

After the preforms have been molded, the bottom former moves away and the first mold 20 opens, as shown, for example, with reference to sections A and B of FIG. 1. The first transfer arm 60, carrying the preforms, then moves to its forward position, as shown, for example, with respect to section C of FIG. 1. In this manner, the preforms are moved into the second mold 40 such that the preforms molded in the first mold cavities 26, 28, 30 are now located within the second mold cavities 46, 48, 50, respectively. As can be appreciated, the motion of the first transfer arm 60 also inverts the preforms such that the bottoms of the preforms are now located toward the bottom of the second mold 40.

Once the preforms are located within the second mold 40, the second mold moves to its closed position, as shown, for example, with reference to section A of FIG. 1. A bottle forming head, not shown, then moves over the second mold cavities 46, 48, 50 and causes the preforms to expand into the second mold cavities, and thus assume the shape of the final bottle in a conventional manner. The bottle forming head may be of the type associated with a conventional "blow and blow" process or a conventional "press and blow" process or any other type of bottle forming process.

After the bottles are formed in the second mold 40, the second transfer arm 70 moves over the second mold 40 and engages the necks of the bottles formed therein. Thereafter, the second mold 40 opens, as shown, for example, with respect to section B of FIG. 1, and the second transfer arm 70 moves to its forward position, carrying the completed bottles with it, as shown for example, with respect to sections A and C of FIG. 1 and with respect to the solid line portion of FIG. 2.

After reaching its forward position, the second transfer arm 70 releases the bottles, allowing them to rest on surface 110 which is located adjacent to the conveyor 120. The extendable struts 96 of the swing arm assembly 90 are then extended, causing the bottle engaging member 94 to extend into contact with the bottles, as shown with reference to section A of FIG. 1. The swing arm assembly 90 is then rotated in a counter-clockwise direction, causing the bottles to move onto the conveyor 120 and, thus, be conveyed along the conveyor 120 in the direction 122. This movement of the bottles onto the conveyor may be facilitated by an arcuate guide 112 located on the surface 110.

In the manner described above, the bottle manufacturing machine 10 causes molten glass to be converted into glass bottles. The finished bottles are deposited on the conveyor 120 so that they may be conveyed to other downstream manufacturing stations in a conventional manner.

In a typical bottle manufacturing machine, the timing of each of the sections of the machine is staggered so that molten glass may be fed to the machine in a steady manner and so that conveyor utilization may be optimized. Referring, for example to the bottle manufacturing machine 10 of FIG. 1, it can be seen that each of the sections A, B and C is in a different stage of operation. The sections are typically staggered such that the conveyor 12 will be fully packed (i.e., no significant gaps between bottles) downstream of the bottle manufacturing machine, as shown in FIG. 1.

Due to the staggering described above, one cycle time of a bottle manufacturing machine is generally defined as the time required for all of the sections to deposit a set of bottles (e.g., three, in the example shown in FIG. 1) onto the conveyor 120. As can be appreciated, the bottle manufacturing machine cycle time will be equal to the cycle time of each section. In other words, the time for one cycle of the bottle manufacturing machine will be equal to the time for a section to complete one cycle. Accordingly, each cycle of the bottle manufacturing machine will result in the production of a number of bottles equal to the number of mole sections in the machine multiplied by the number of mold cavities in each section. In the example illustrated in FIG. 1, nine bottles (three sections multiplied by three mold cavities per section) would be manufactured each time that the bottle production machine completes one cycle. Accordingly, the bottle production machine 10 illustrated in FIG. 1 would produce nine bottles per machine cycle.

Referring again to FIG. 1, a bottle inspection station 130 may be located adjacent the conveyor 120 at a location downstream of the bottle manufacturing machine 10. The bottle inspection station 130 may generally include a first imaging device 132 and a second imaging device 134 as shown. The inspection station 130 may also include a light source 136 and a triggering device 138.

In operation, the bottle imaging system 130 may be used to analyze the bottles being conveyed past the imaging system for dimensional attributes and/or for flaws which may exist in the bottles. Specifically, the triggering device 138 may be used to detect when a bottle, e.g., the bottle 150 in FIG. 1, has entered a target area 142. When a bottle is detected in the target area 142, images of the bottle 150 may then be acquired by the imaging devices 132, 134 and analyzed by a remote computer, not shown, in order, for example, to inspect the bottle for flaws. When the next bottle, e.g., the bottle 152, FIG. 1, enters the target area, the process is repeated and so on for each bottle on the conveyor 130. Accordingly, each of the bottles being conveyed on the conveyor 130 may be inspected by the inspection station 130.

The inspection station 130 may be configured and operate in a manner as disclosed in the Burns et al. and Lucas patents previously referenced.

When a bottle, such as the bottle 150, is inspected by the bottle inspection station 130, it is desirable to be able to correlate the bottle being inspected to the mold cavity of origin in which the bottle was manufactured. This information is useful, for example, because some types of defects detected by the inspection station 130 may be caused by a defect in the mold cavity; accordingly, the presence of a defect in an inspected bottle can sometimes indicate a problem with a particular mold cavity in the bottle manufacturing machine.

As can be appreciated, bottles being conveyed past the bottle inspection station 130 will arrive in a particular order with respect to the mold cavity of origin of each bottle. The bottle manufacturing machine 10 of FIG. 1 may, for example, cause bottles to be arranged in the following order relative to the mold cavity of origin for each bottle: 46B, 48B, 50B, 46A, 48A, 50A, 46C, 48C, 50C. Accordingly, bottles will pass through the bottle inspection system target area 142 in this repeating sequence.

In order to determine the mold cavity of origin for a particular bottle located in the target area 142, prior inspection devices have used a mechanical detection device which sends a pulse signal to the inspection device remote computer each time that the bottle manufacturing machine completes a cycle. Before the inspection device is initially placed into operation, the mold cavity of origin is determined for the bottle located in the target area 142 when the mechanical detection device pulse signal arrives. This determination may be made, for example, by reading mold indicia which may appear on the bottle, or by visually following the bottles while running the bottle manufacturing machine at a very low speed. The particular bottle which is located within the target area 142 when the signal pulse arrives depends, among other things, upon the distance between the inspection station 130 and the bottle production machine 10.

Once the arrival of the pulse signal is correlated to a particular mold cavity of origin, the mold cavity of origin for each bottle can then be readily determined by merely counting the bottles beginning with the pulse signal and comparing this count to the known predetermined mold cavity of origin sequence associated with the particular bottle manufacturing machine. With reference to FIG. 1, if, for example, the bottle 150 is located in the target area 142 when the signal pulse arrives and if the bottle 150 was manufactured in the mold cavity 48C, then it will be known that each time the signal pulse arrives, the bottle being imaged when the pulse arrives was manufactured in the mold cavity 48C. As can be appreciated, it can also readily be determined that the next bottle imaged was manufactured in the mold cavity 50C, the next was manufactured in mold cavity 46B, and so on. Accordingly, if the inspection system detects a defect in a particular bottle, the defective bottle can readily be correlated to its mold cavity of origin and repairs and/or adjustments may be made to the mold cavity as appropriate.

Machine Cycle Detection

As can be appreciated, the conventional inspection system, as described above, requires the use of a mechanical detection device in order to sense the cycling of the bottle manufacturing machine and to send signal pulses to the inspection system remote computer. The use of a mechanical detection device, however, is disadvantageous in that such mechanical detection devices generally require mechanical interaction with a moving part or parts of the bottle production machine and, thus, are subjected to mechanical wear. Because a mechanical detection device represents an additional component of the inspection system, the use of a mechanical detection device also adds to the expense of the overall inspection system.

These disadvantages are overcome by the present invention as will now be described in detail. With reference to FIG. 1, it can be appreciated that, while imaging the bottle 150 in the target area 142, the second imaging device 134 is also able to image a portion of the bottle manufacturing machine 10 in the background. In this manner, the remote computer connected to the second imaging device 134 is able to detect the movement of a selected part of the bottle manufacturing machine 10 and, thus, detect when the machine cycles. This avoids the need for a mechanical detection device and, thus, also avoids the disadvantages associated with mechanical detection devices as described above.

Although it is possible to detect the movement of many different components of the bottle manufacturing machine, the detection method will now be described, for exemplary purposes, with respect to the second transfer arm assembly 70A of section A of the bottle manufacturing machine 10. As can be appreciated from FIG. 1, the second transfer arm 70A is readily visible to the second imaging device 134.

As previously described, the second transfer arm 70A moves between a forward position, as shown with respect to sections A and C of FIG. 1 and with respect to the solid line portion of FIG. 2, and a rearward position as shown with respect to section B of FIG. 1 and with respect to the phantom line portion of FIG. 2. Second transfer arm 70A dwells in its forward position for most of a machine cycle. Once per cycle, however, the second transfer arm moves to its rearward position. Accordingly, the timing of the bottle manufacturing machine 10 may be determined by detecting the movement of the second transfer arm to its rearward position.

Figure 3:
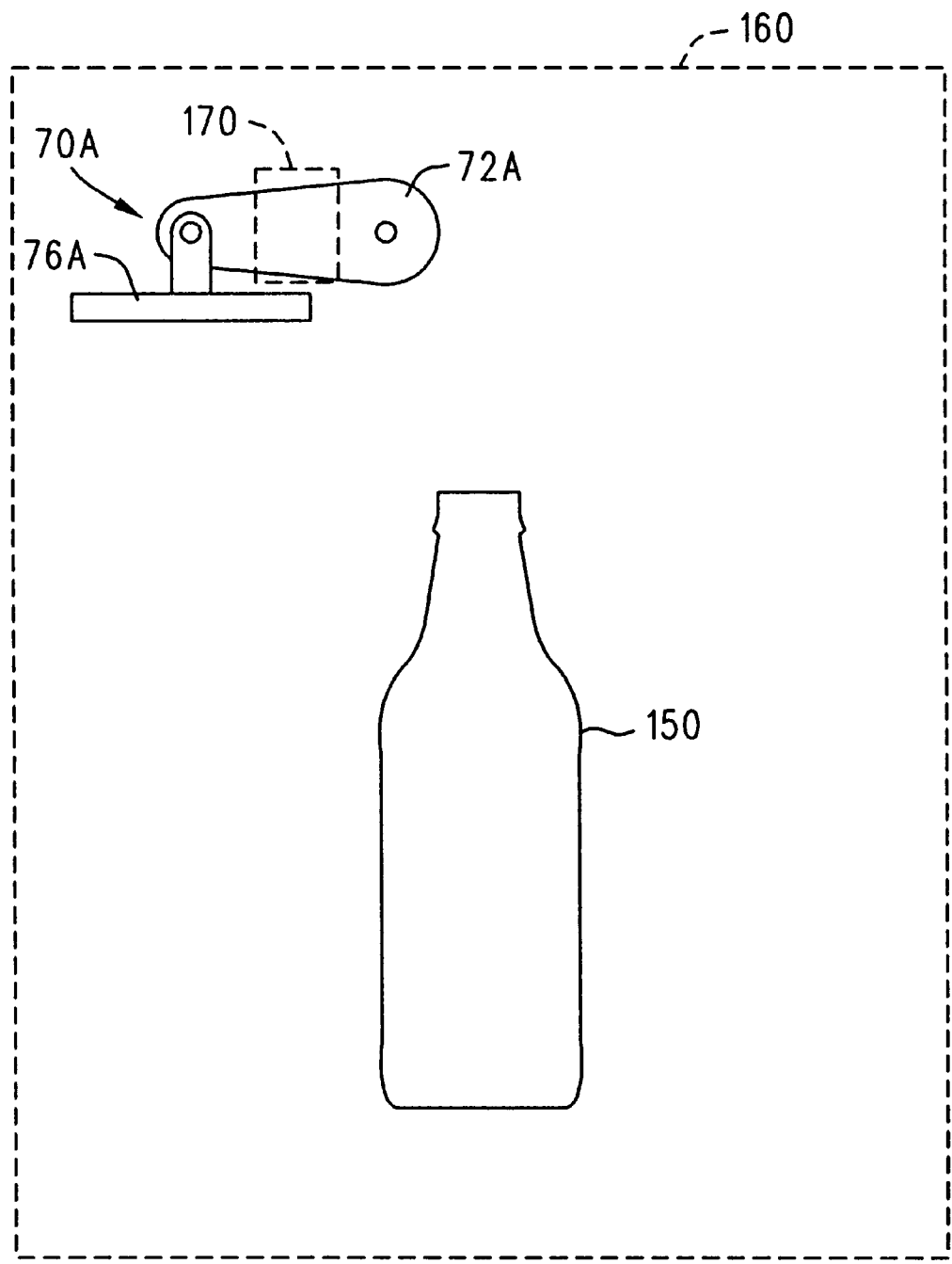
FIG. 3 is a schematic view illustrating the image generated by the inspection station of FIG. 1 when a portion of the bottle manufacturing machine is in a first position.

FIG. 3 schematically illustrates the image 160 generated by the second imaging device 134 when the second transfer arm 70A is in its forward position. As can be seen, the bottle 150, which is located in the target area 142, FIG. 1, is imaged within the image 160. As can further be seen, the second transfer arm 70A is also imaged within the image 160.

Figure 4:
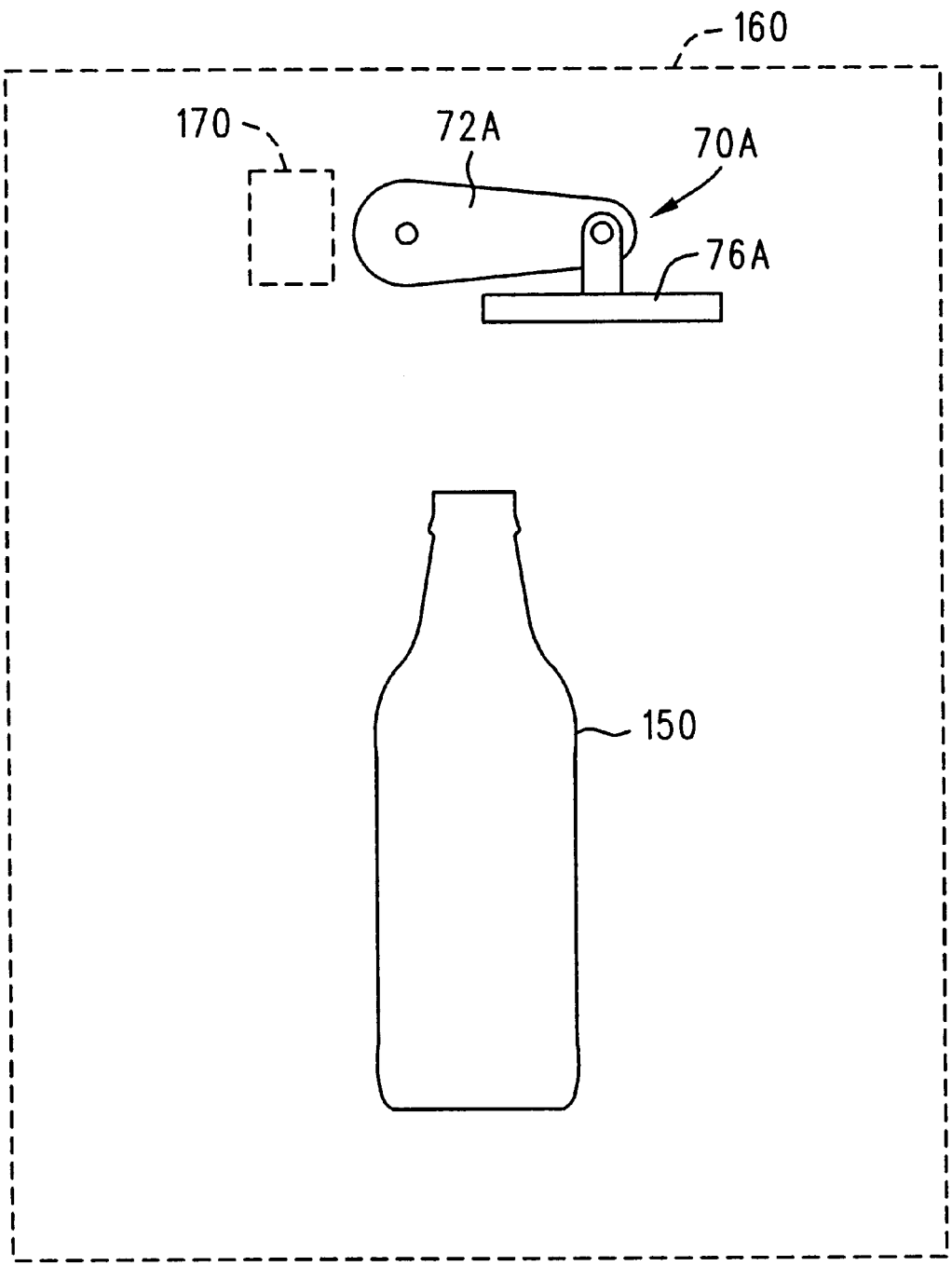
FIG. 4 is a schematic view, similar to FIG. 3, illustrating the image generated by the inspection station of FIG. 1 when the portion of the bottle manufacturing machine is in a second position.

With further reference to FIG. 3, an image target area 170 may be located within the image 160 such that the image target area 170 coincides with the location of the second transfer arm pivot arm member 72A when the second transfer arm 70A is in its forward position. FIG. 4 schematically illustrates the image 160 generated by the second imaging device 134 when the second transfer arm 70A is in its rearward position. As can be seen from FIG. 4, the second transfer arm pivot arm member 72A is no longer located within the image target area 170. Accordingly, the remote computer attached to the second imaging device 134 is able to detect when the second transfer arm 70A is in its forward position by detecting the presence of the second transfer arm pivot arm member 72A within the image target area 170. Conversely, when the second transfer arm pivot arm member 72A is not detected within the image target area 170, as shown in FIG. 3, the remote computer is able to detect that the second transfer arm 70A is in its rearward position.

In operation, each time a bottle enters the target area 142, FIG. 1, the triggering device 138 senses the presence of the bottle and causes an image of the bottle to be generated by each of the imaging devices 132, 134. Each time that a bottle is imaged in this manner, the image 160, FIGS. 3 and 4, generated by the second imaging device is also analyzed to determine whether the second transfer arm pivot arm member 72A is present within the image target area 170. So long as the pivot arm member 72A is detected in the image target area 170, no action is taken. The first time, however, that the pivot arm member is not detected within the image target area, the remote computer may generate a new cycle signal, indicating that a new cycle has begun. In this manner, the remote computer is able to determine when a new bottle manufacturing machine cycle begins without the need for a mechanical detection device.

It is noted that other portions of the bottle manufacturing machine 10, in addition to the second transfer arm assembly 70A, may also be imaged within the image 160 but have not been shown in FIGS. 3 and 4 for purposes of clarity.

The process described above is illustrated in flow chart form in FIG. 5.

Figure 5:
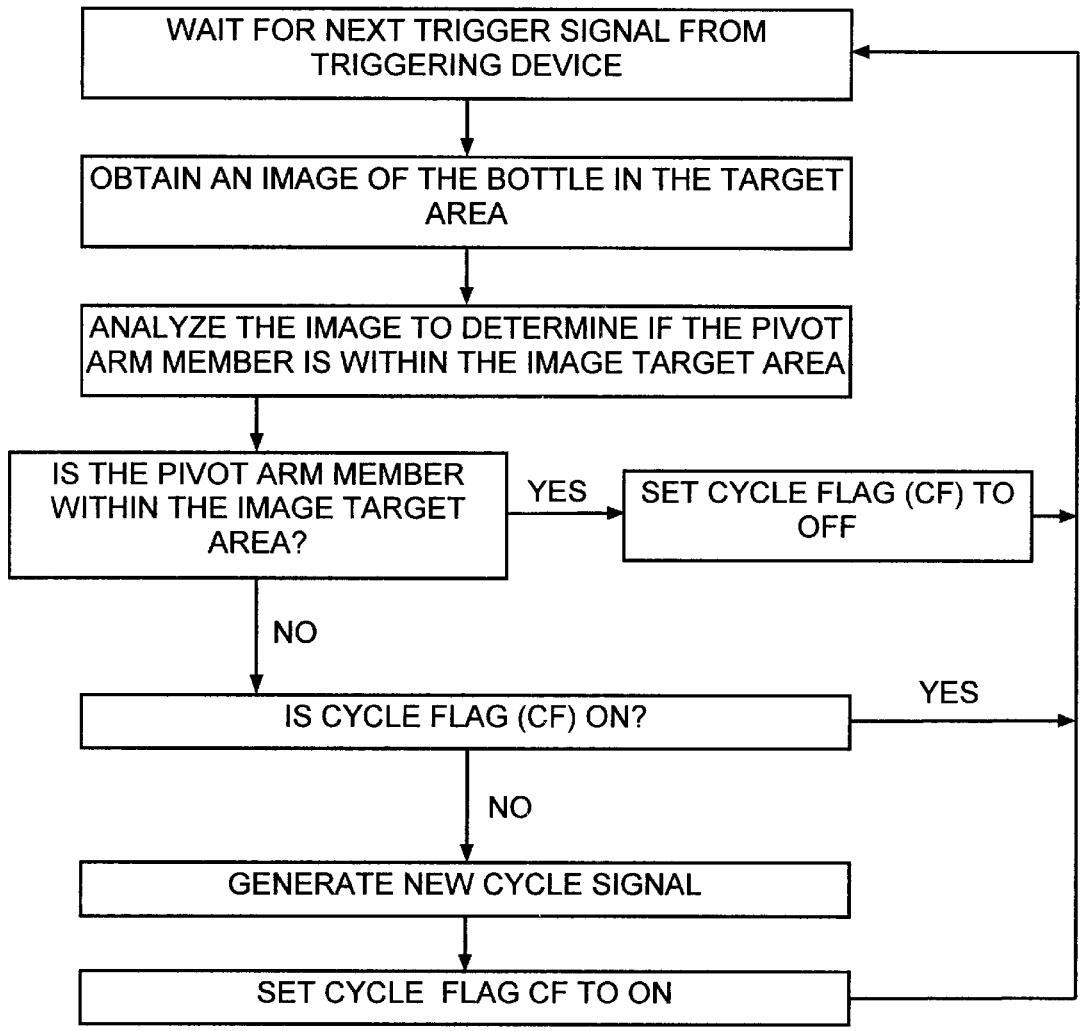
FIG. 5 is a flow chart illustrating a method according to the present invention.

It is noted that the second transfer arm 70A may remain in its second position while more than bottle moves through the target area 142. Accordingly, multiple trigger signals from the triggering device may occur while the transfer arm 70A is in its rearward position. In order to prevent false new cycle signals from being generated, the present method may include a procedure for ensuring that a new cycle signal is generated only the first time that the transfer arm 70A is found to be missing from the target area 170. With reference to FIG. 5, in order to accomplish this, a cycle flag "CF" may be used. Specifically, a new cycle signal will be generated only when the pivot arm member 72A is not detected within the target area 170 and the cycle flag "CF" is off. Each time that a new cycle signal is generated, the cycle flag "CF" is turned on. The cycle flag is returned to the off condition only after the pivot arm member 72A returns to the target area 170. Accordingly, the method described above will ensure that a new cycle signal is generated only the first time in each cycle that the pivot arm member 72A is missing from the target area 170.

Mold Cavity of Origin Determination

As described above, in previous bottle detection methods, the current bottle being inspected is correlated to its mold cavity of origin by counting the number of bottles which have been inspected since the new cycle signal was generated. For example (using the mold cavity of origin order previously set forth, ie.: 46B, 48B, 50B, 46A, 48A, 50A, 46C, 48C, 50C) it may be determined that the bottle being imaged when the new cycle signal is generated was, for example, formed in the mold cavity 48C. Accordingly, each time that a new cycle signal is generated, the bottle currently being imaged will have been generated in the mold cavity 48C. As can be appreciated, the other bottles imaged by the inspection station 130 may be correlated to their respective mold cavities of origin by counting the number of bottles imaged since the new cycle signal was generated.

If, for example, the current bottle being imaged is the fourth bottle imaged after the new cycle signal, then the bottle may be assigned the number four. The bottle number four may then be correlated to the mold cavity 50B, since the mold cavity 50B is the fourth mold cavity following the new cycle signal mold cavity 48C, given the example mold order set forth above.

One problem with the method described above is that bottles sometimes fall down or are missing from the conveyor. A fallen or missing bottle will not trigger the triggering device 138 and will, thus, not cause the inspection system 130 to generate an image. This missing image, in turn, will cause the counting method described above to assign the wrong mold cavities of origin to the bottles being inspected.

To remedy this problem, the present invention includes a mold cavity of origin correlation method which relies upon timing rather than upon counting as will now be described in detail.

According to the present method, a cycle time length "CL" is first calculated for the bottle manufacturing machine 10. To calculate the cycle time length, a timer may be used to measure the elapsed time between two consecutive new cycle signals. The timer may, for example, be read and then reset to zero each time that a new cycle signal is generated. The cycle time length is then divided by the number of mold cavities to determine a bottle interval time "BIT". As can be appreciated, if no bottles are fallen or missing, then a new bottle should arrive within the conveyor target area 142, FIG. 1, as each bottle interval time expires.

In order to assign a number to a bottle being imaged, the timer value (which is reset each time that a new cycle signal is generated) is first recorded when the bottle is imaged. As can be appreciated, this recorded time will represent the elapsed time between the last new cycle signal and the arrival of the current bottle in the conveyor target area 142. The recorded timer value is then divided by the previously determined bottle interval time "BIT" to determine the number of the currently imaged bottle. This number may then be correlated to the mold cavity of origin depending upon the mold cavity order of the bottle manufacturing machine in a manner as described previously. As can be appreciated, the bottle being imaged when the new cycle signal is generated (which, in the above example, was formed in the mold cavity 48C) will be assigned the number zero, since the timer value will be zero at this time.

Continuing with the example set forth previously, if a cycle time of, for example, nine seconds is measured, then a bottle interval time of 1 second results (nine second cycle time divided by nine mold cavities). If a bottle arrives within the target area 142 at a time equal to five seconds, then a bottle number of five will be calculated (five seconds divided by the bottle interval time of 1 second). The bottle number five may then be correlated to mold cavity of origin 46A, since the mold cavity 46A is the fifth mold cavity after the new cycle signal mold cavity 48C, given the example mold cavity order set forth above.

The present method, thus, correlates imaged bottles based upon their time of arrival within the target area 142 and not based upon their sequence of arrival as in prior methods. As can be appreciated, the present method is capable of accurately correlating an imaged bottle to its mold cavity of origin even if one or more preceding bottles has fallen or is missing.

It is noted that, so long as the bottles being conveyed on the conveyor 120 are uniformly spaced, the calculated bottle number, as described above, will be a whole number. In practice, however, bottles are often distributed along the conveyor in a non-uniform manner, i.e., the spacing between adjacent bottles on the conveyor is not uniform. Such non-uniform spacing will result in the calculated bottle number being a non-whole number. In order to address this problem, non-whole bottle numbers may merely be rounded to the nearest whole number in order to correlate the imaged bottle to its mold of origin. It has been found that this rounding procedure functions without ambiguity so long as the average spacing between bottles is less than one-half of a bottle width, as is typical in most bottle manufacturing situations.

Figure 6:
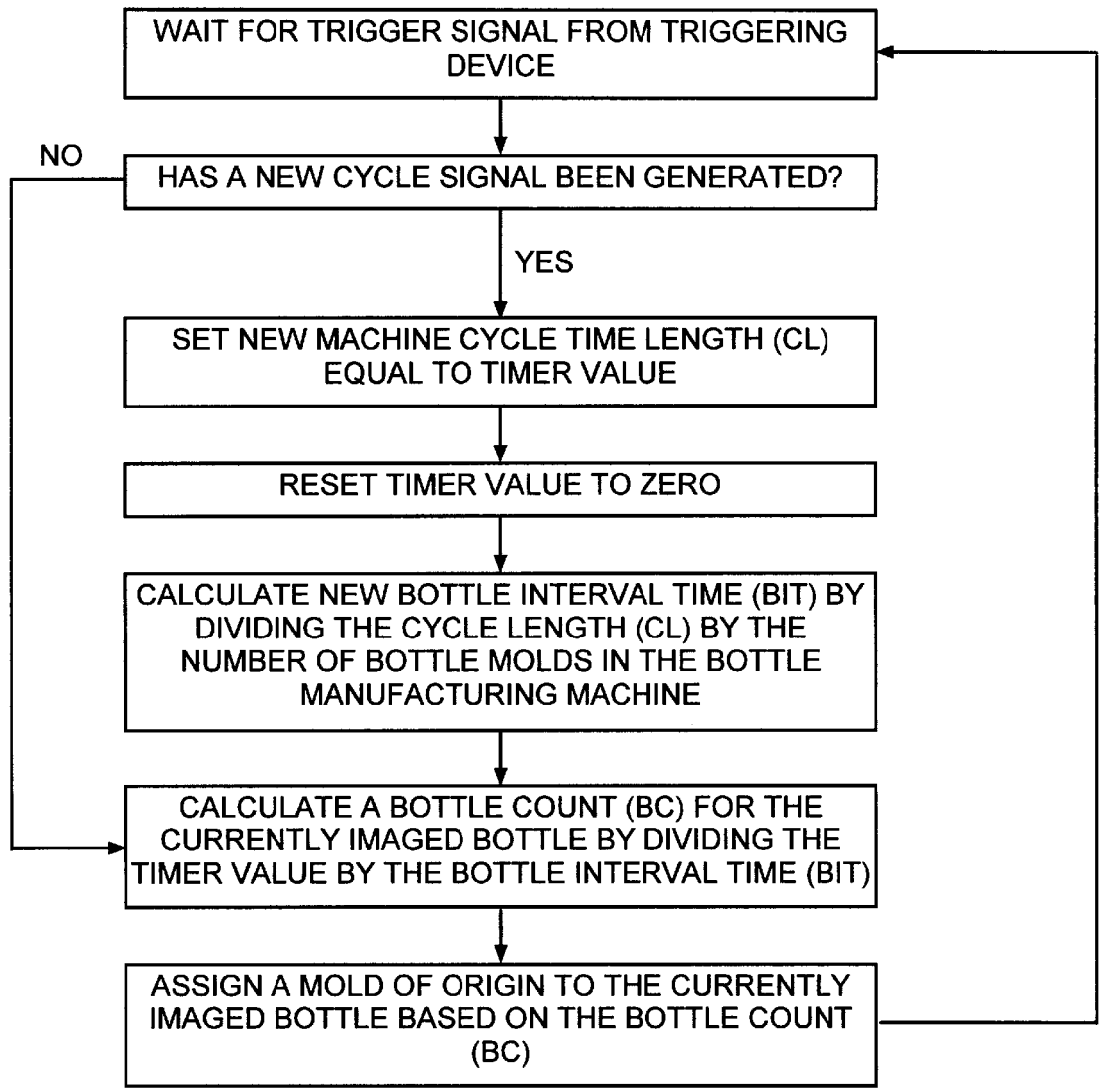
FIG. 6 is a flow chart illustrating a second method according to the present invention.

The present method is illustrated in flow-chart format in FIG. 6. It is noted that the cycle length may be recalculated each time that a new cycle signal is generated, as shown in FIG. 6. In this manner, the cycle length will remain accurate even if the bottle manufacturing machine 10 changes speed over time during its operation.

It is noted that it is often desirable to maintain a running count of the number of bottles produced by a bottle manufacturing machine. Typically, such a count is maintained by counting the number of times that the triggering device 138 has been triggered. As can be appreciated, however, such a count will not include bottles which have fallen or are missing and will, therefore, not necessarily render an accurate count of the number of bottles produced by the machine 10.

According to the present method, the number of times that the triggering device 138 has been triggered may also be counted. In order to compensate for the fallen bottle problem described above, however, the present method may also count the number of bottles which are missing, and add the number of missing bottles to the trigger count in order to determine the actual number of bottles produced. As can be appreciated, the correlation methodology described above can readily determine when a bottle is missing by looking for a trigger signal from the triggering device 138 each time that a bottle is due to appear. If no trigger occurs at the expected time, then a bottle is missing. Accordingly, the present method is further advantageous in that it is able to produce an accurate count of bottles actually produced by the machine 10.

The software code for accomplishing the above methods is set forth in the previously reference Microfiche Apppendix and forms a part of this disclosure.

It is noted that, although described with respect to a bottle production facility for exemplary purposes, the above methods could easily be applied to any manufacturing environment where it is desirable to correlate an object being inspected to its point of origin.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method of inspecting objects with an imaging device which is positioned adjacent a conveyor along which said objects are conveyed at a location downstream from a machine for manufacturing said objects, said method comprising:

obtaining an image with said imaging device, wherein said image includes at least one of said objects in a first area of said image and includes at least a portion of said machine in a second area of said image;

performing an analysis of at least a portion of said second area of said image;

determining an operating condition of said machine based upon said analysis.

2. The method of claim 1 wherein said machine is a bottle forming machine.

3. The method of claim 1 wherein said step of performing an analysis includes making a determination as to whether said machine has cycled.

4. The method of claim 3 wherein said machine includes a plurality of manufacturing stations therein and wherein each of said objects is manufactured by one of said plurality of manufacturing stations.

5. The method of claim 4 and including the further step of correlating an object imaged by said imaging device to a particular one of said manufacturing stations which manufactured said object based upon said determination.

6. The method of claim 5 wherein said machine repeatedly cycles in order to manufacture said objects, wherein one object is manufactured in each of said plurality of manufacturing stations during each cycle of said machine and wherein said step of correlating includes a step of determining the length of time taken for said machine to complete a cycle.

7. The method of claim 6 wherein said step of correlating further comprises determining an object interval time by dividing said length of time by the number of manufacturing stations associated with said machine.

8. The method of claim 7 wherein said step of correlating further includes a step of measuring the elapsed time between the time of the last cycle of said machine and the time that said image is obtained.

9. The method of claim 8 wherein said step of correlating further includes dividing said elapsed time by said object interval time.

10. The method of claim 1 wherein said step of performing an analysis comprises evaluating the position of said at least a portion of said machine.

11. A method of inspecting products comprising the steps of:

providing a manufacturing machine including a plurality of manufacturing stations associated therewith;

cycling said manufacturing machine to produce a plurality of products, wherein one product is manufactured in each of said plurality of manufacturing stations during each cycle of said manufacturing machine;

transferring each of said plurality of products to a conveyor after being manufactured by said manufacturing machine;

conveying each of said plurality of products along said conveyor;

inspecting at least one of said plurality of products as it is being conveyed along said conveyor;

determining the length of time taken for said manufacturing machine to complete a cycle;

correlating said at least one of said plurality of products to the manufacturing station which manufactured said at least one of said plurality of products based upon said length of time.

12. The method of claim 11 including the further step of providing an imaging device adjacent said conveyor and wherein said step of determining comprises obtaining an image of at least a portion of said manufacturing machine with said imaging device.

13. The method of claim 12 wherein said step of inspecting comprises obtaining an image of said at least one of said plurality of products with said imaging device.

14. The method of claim 13 wherein said step of determining further comprises evaluating said image of at least a portion of said manufacturing machine to determine the position of said at least a portion of said manufacturing machine.

15. The method of claim 11 wherein said manufacturing machine is a bottle forming machine.

16. The method of claim 11 wherein said step of correlating includes a step of determining an object interval time by dividing said length of time by the number of manufacturing stations associated with said manufacturing machine.

17. The method of claim 16 wherein said step of correlating further includes a step of measuring the elapsed time between the time of the last cycle of said manufacturing machine and the time that said at least one of said plurality of products is inspected.

18. The method of claim 17 wherein said step of correlating further includes dividing said elapsed time by said object interval time.

* * * * *